United States Patent [19]
Noweck et al.

[11] Patent Number: 5,883,272
[45] Date of Patent: Mar. 16, 1999

[54] ALUMINOSILICATE CARRIER FOR METATHESIS CATALYSTS

[75] Inventors: Klaus Noweck, Brunsbüttel; Andreas Hoffmann, Hannover, both of Germany

[73] Assignee: RWE-DEA Aktiengesellschaft fur Mineraloel und Chemie, Germany

[21] Appl. No.: 849,972

[22] PCT Filed: Dec. 19, 1995

[86] PCT No.: PCT/DE95/01846

§ 371 Date: Jun. 20, 1997

§ 102(e) Date: Jun. 20, 1997

[87] PCT Pub. No.: WO96/19287

PCT Pub. Date: Jun. 27, 1996

[30] Foreign Application Priority Data

Dec. 21, 1994 [DE] Germany .......................... 44 45 608.5

[51] Int. Cl.$^6$ .................................................. C07C 51/00
[52] U.S. Cl. .......................... 554/163; 554/162; 554/161; 502/102; 502/232; 502/240; 502/241; 560/205; 585/502; 585/520; 585/530; 585/533
[58] Field of Search ..................... 554/161, 162, 554/163; 585/502, 520, 530, 533; 502/102, 232, 240, 241; 560/205

[56] References Cited

U.S. PATENT DOCUMENTS 5,143,885  9/1992  Warwel et al. .......................... 502/202

FOREIGN PATENT DOCUMENTS 0053499  6/1982  European Pat. Off. .
4107056  9/1992  Germany .

OTHER PUBLICATIONS

M. Siebeijn, et al., "Technological and Economical Aspects of the Metathesis of Unsaturated Esters," JAOCS, vol. 71, No. 6, Jun. 1994, pp. 553–561.
Sibeijn et al., JAOCS, vol. 71, No. 6, pp. 553–561 1994.
Suzuki et al., Chem. abstr. of EP–53399, 1982.

*Primary Examiner*—Gary Geist
*Assistant Examiner*—Deborah D. Carr
*Attorney, Agent, or Firm*—Madan & Morris, PLLC

[57] ABSTRACT

Rhenium oxide catalysts carried on aluminium silicates, if required with added boric oxide, tungsten oxide, molybdenum oxide or vanadium oxide for the metathesis of olefins and functionalised olefins, in particular of carboxylic acid esters, are provided, whereby the carrier material was hydrothermally treated.

19 Claims, No Drawings

ALUMINOSILICATE CARRIER FOR METATHESIS CATALYSTS

This application is a 371 of PCT/DE95/01846 filed Dec. 19, 1995.

The invention relates to rhenium oxide catalysts carried on hydrothermally treated aluminium silicates, if required with added boric oxide, tungsten oxide, molybdenum oxide or vanadium oxide for the metathesis of olefins and functionalised olefins.

In industrial technology, the metathesis of olefinic hydrocarbons is used in the production of special olefins, dienes and polyenes and unsaturated polymers. Polymers are made by ring-opening metathetic polymerisation (ROMP). Metathesis reactions can be carried out both energy-efficiently at room temperature and at lower or higher temperatures.

Olefins with functional groups, too, are subject to metathesis reaction, as long as suitable catalysts are used. In this, the metathesis of unsaturated fatty acid methyl esters is especially significant. By the transition-metal-catalysed metathesis of these esters, which in industry are produced by transesterification of natural vegetable oils and animal fats with low alcohols, in particular with methanol in the 100000 t scale, important industrial chemicals for the tenside and plastics sectors as well as for the production of high-grade lubricants and a multitude of chemical-technical intermediary products and fine chemicals can be obtained. The principal significance of the metathesis of unsaturated fatty acid esters for industrial applications has been described in various publications, c.f. for example M. Sibeijn et al.: "Technological and Economical Aspects of the Metathesis of Unsaturated Esters" in Journal of the American Oil Chemists' Society vol 71, issue 6, p. 553 (1994).

As a result of the so-called homometathesis of unsaturated fatty acid esters, long-chain dicarboxylic acid esters are obtained:

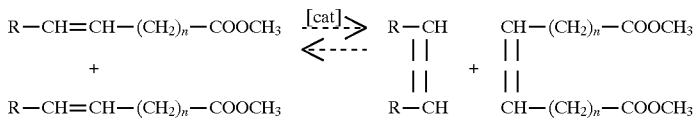

As a result of the so-called co-metathesis of unsaturated fatty acid esters with olefins according to

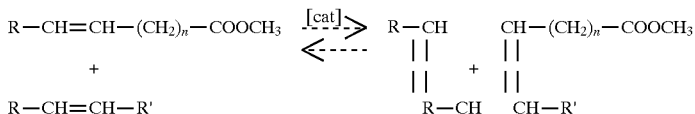

the lengths of the chains and/or structures of fatty acid esters, depending on the olefin used, are changed. For example, it is possible to transfer unsaturated $C_{18}$ fatty acid methyl esters made from rape-, sunflower- or soy oil or from tallow—by way of co-metathesis with petrochemical $C_4$- to $C_6$-olefins (butenes, pentenes, hexenes)—into medium-chain fatty acid esters of the so-called Laurie-range with chain lengths in particular of 12 to 14.

Esters with such chain lengths have hitherto been obtained in industry from tropical oils (coconut and palm kernel oil); they are used in the manufacture of fatty alcohols for the production of tensides.

Through co-metathesis of unsaturated fatty acid esters with ethylene, terminally unsaturated esters are obtained which can be used for the production of dicarboxylic acids of different chain lengths and of organic intermediate products and fine chemicals of the most varied kind. By co-metathesis of unsaturated fatty acid esters with branched olefins, branched unsaturated fatty acid esters are obtained which are of significance in the production of impregnating agents and special lubricants in technical applications and in cosmetics.

As catalysts for the metathesis reactions, preferably $Re_2O_7$-carrier contacts are used which are activated with metallo-organic compounds such as tin alkyls or lead alkyls of the general formulae $SnR_4$ or $PbR_4$. In this, a general catalyst is $Re_2O_7/\gamma\text{-}Al_2O_3$, activated with stannic alkyls. Apart from $\gamma\text{-}Al_2O_3$ as a carrier substance for $Re_2O_7$, aluminium silicate carriers are also known from the literature.

In FR-A-2 521 872 the carrier contains preferably only 10 to 30% by volume $SiO_2$. Here organic lead compounds of the general formula $PbR_4$ serve as activators. In NL-A-84 03 051 the metathesis is carried out on carrier catalysts rich in $SiO_2$. In the carrier, the $Re_2O_7/\gamma\text{-}Al_2O_3$ $SiO_2$ catalysts contain 65 to 90% by weight $SiO_2$. Preferably stannic ethyl and stannic butyl are used as activators. In EP-B1-0 444 265, aluminium silicates with 40% by weight of $SiO_2$ are used as carriers. Here, activation is with aluminium alkyl alcoholates of the general formula $AlR_nR'_m$ (with n+m=3, R=alkyl and R'=alcoholate) or polymer alkylaluminoxanes.

Production of catalysts is by impregnating the carriers with solutions of ammonium perrhenate, subsequent drying and calcination in the airstream at increased temperatures. According to EP-B1-0 444 264 an increase in catalytic activity is achieved in those instances when the $Al_2O_3$—$SiO_2$ carriers are not only impregnated with ammonium perrhenate ($NH_4ReO_4$) but also with boric acid ($H_3BO_3$) and in this way catalysts of the composition $B_2O_3$—$Re_2O_7$ $Al_2O_3$—$SiO_2$ are produced. After drying and heating, the oxidic catalyst is created. Activation is with organotin compounds as co-catalysts.

All processes from the literature share the central problem that for practical application of the catalysts, for the metathesis of functionalised olefins, in particular of unsaturated carboxylic acid esters, the catalysts must be employed in high concentrations, in order to result in a useful transformation. Thus, economic application of the metathesis reaction of unsaturated carboxylic acid esters is not possible.

It is the object of the present invention to develop more active catalysts for the metathesis. The aim is to achieve a high olefin yield with the smallest possible rhenium contents—rhenium content determines the price level of the process. Above all, the catalysts should enable a higher transformation and a higher yield during metathesis of unsaturated fatty acid esters.

Apart from the high catalytic activity of the catalysts according to the invention, their particular advantage is their multiple reusability following thermal reactivation. This advantage is decisive for technical applications. This characteristic is surprising, because according to the state of the art regarding recyclability of rhenium-oxide carrier-catalysts during metathesis of unsaturated carboxylic acid esters, nothing is known.

This object is achieved according to the invention by the use of rhenium oxide catalysts carried on aluminium silicates, if required with added boric oxide, tungsten oxide, molybdenum oxide or vanadium oxide, whereby the aluminium silicate carrier is made from a silicon compound such as silicic acid which serves as an $SiO_2$ supplier and an aluminium compound in aqueous environment, and the aluminium silicate/water mixture is subjected to temperature treatment during and/or after, preferably after, the reaction of the silicon compound with the aluminium compound. These catalysts are preferred for the metathesis of olefins and functionalised olefins, in particular unsaturated carboxylic acid esters.

DE-Cl-38 39 580 describes a process for the production of such a hydrothermally treated catalyst carrier on the basis of an aluminium silicate with 0.5 to 50% by weight $SiO_2$ and if necessary 0.5 to 2% by weight $La_2O_3$ by mixing an aluminium compound with a silicic acid compound in an aqueous environment, if required under simultaneous or subsequent addition of a soluble lanthanum compound, as well as drying and if required calcination of the product obtained up to 24 hours at a temperature of up to 1100° C.

The aluminium silicates used as catalyst carrier material according to the invention are made from an $SiO_2$ supplier and an aluminium compound, preferably in an aqueous environment. Preferably the silicon compound as $SiO_2$ supplier is a silicic acid; for example it can be an orthosilicic acid cleaned by way of ion exchangers The aluminium alcoholate is hydrolysed for example with water cleaned by way of ion exchangers. In this at the same time or subsequently, the orthosilicic acid, for example cleaned by way of ion exchangers, is added to it or mixed with it. Preferably C2- to C20-aluminium alcoholates are used as an aluminium component reactive to water and/or silicic acid The freed alcohols are removed from the reaction mixture after reaction.

Hydrothermal treatment is a significant part of the process of aluminium silicate production for the carriers according to the invention and consists in temperature treatment during and/or after, preferably after, the reaction of the silicic acid compound with the aluminium compound In this, the aluminium silicate/water mixture is subjected to a temperature of 90° to 235° C., preferably of 150° to 200° C. for 0.5 to 20 hours, preferably for a duration of 1 to 5 hours.

The catalyst carriers obtained in this way are of a high chemical purity, have a homogenous distribution of $Al_2O_3$ and $SiO_2$, a high specific surface (depending on the $SiO_2$ content) and excellent surface stability, defined pore distribution, pore diameter and high specific activities.

TABLE 1

Aluminium silicates altered hydrothermally

| $SiO_2$ content [% by weight] | Surface [m²/g] | Pore volume [ml/g] | Pore radius [Å] | Acidity [$10^{-4}$ mmol n-butylamine/m²] |
|---|---|---|---|---|
| 1.5 | 234 | 0.7 | 54 | 12.8 |
| 10 | 350 | 1.17 | 45 | 19.3 |
| 20 | 365 | 1.26 | 54 | 20.3 |
| 30 | 310 | 1.54 | 77 | 26.4 |

TABLE 1-continued

Aluminium silicates altered hydrothermally

| $SiO_2$ content [% by weight] | Surface [m²/g] | Pore volume [ml/g] | Pore radius [Å] | Acidity [$10^{-4}$ mmol n-butylamine/m²] |
|---|---|---|---|---|
| 40 | 295 | 1.42 | 78 | 23.1 |
| 50 | 302 | 1.17 | 66 | 17.9 |

Pore volumes and pore radia were determined by means of the mercury penetration porosimetry (Autopore II 9220, Micromeritics porosimeter). In order to determine the specific surface, a BET adsorption isotherm ($N_2$) was taken with the Gemini 2360/2375 of the enterprise Micromeritics.

The $SiO_2$ contents of the $Al_2O_3$—$SiO_2$ carriers ranged from 1.5 to 50% by weight, preferably 5 to 30% by weight. On average, as a result of hydrothermal treatment, pore volume, pore radius and acidity changed, as was shown by a comparison with aluminium silicates made without hydrothermal treatment. The increase in acidity correlates with the increased catalytic activity.

TABLE 2

Aluminium silicates not altered hydrothermally

| $SiO_2$ content [% by weight] | Surface [m²/g] | Pore volume [ml/g] | Pore radius [Å] | Acidity [$10^{-4}$ mmol n-butylamine/m²] |
|---|---|---|---|---|
| 1.5 | 270 | 0.53 | 31 | 9.6 |
| 10 | 370 | 0.56 | 27 | 14.7 |
| 20 | 383 | 0.68 | 31 | 16.4 |
| 30 | 448 | 0.53 | 29 | 16.7 |
| 40 | 456 | 0.71 | 35 | 20.2 |
| 50 | 452 | 0.6 | 33 | 14.8 |

In a further embodiment of the invention, the $Al_2O_3$—$SiO_2$ carrier can additionally contain 2 to 10% by weight, in particular 3 to 8% by weight boric oxides, molybdenum oxides, tungsten oxides and vanadium oxides. $Re_2O_7$ content is between 0.5 and 10% by weight, preferably between 1 and 5% by weight in relation to the carrier.

In the carrier process, rhenium and boron, tungsten, molybdenum or vanadium are applied to the aluminium silicate. This impregnation takes place for example by bringing into contact Re compounds in a solution such as ammonium perrhenate and if required soluble boron, tungsten, molybdenum or vanadium compounds into contact with the finished aluminium silicate. After drying and heating, the oxidic catalyst is created. The components of the catalyst can either be applied together, e.g. in one or two impregnation steps, or after each other, by twice drying and heating the catalyst material, that is to say after applying the first component and after applying the second component.

In a further modification of the process for producing the catalysts according to the invention, water-soluble compounds of Re and if required boron, tungsten, molybdenum or vanadium are added either during hydrolysis of the aluminium compound or when adding silicic acid. Then the finished catalyst is subjected to the heat treatment according to the invention.

The optionally used activator is either added to the reaction together with the educts, or else prior to the reaction with the olefins added to the readily prepared $Re_2O_7$—($B_2O_3$, $MoO_3$, $Wo_3$ or $V_2O_5$)/$Al_2O_3$—$SiO_2$ carrier catalyst, or it is impregnated.

The catalysts can be used as a powder, granulate, extrudate or as a honeycomb structure. Catalysts are preferably used in powder form or in extrudate form.

Metathesis of olefinic hydrocarbons does not require an activator apart from the catalysts according to the invention. However, during metathesis of functionalised olefins or during co-metathesis of olefins and functionalised olefins, the use of an activator is necessary. Functionalised olefins in the sense of the invention are: unsaturated esters, ethers, halogen- and nitrogen compounds, ketones as well as derived alcohols and derived carboxylic acids. Organotin compounds, preferably stannic alkyl of the formula. $SnR_4$, are suitable activators, whereby R=alkyl with 1 to 8 carbon atoms. Examples of R include methyl, ethyl, isopropyl and n-butyl. The activator is preferably used in such quantities that the molar ratio of $Re_2O_7:SnR_4$ is at 5:1 to 1:5. In particular a molar ratio of 2:1 to 1:2 is preferred.

Catalysts according to the invention can be recycled after reactivation. To this effect, the catalysts used in catalysis are first of all separated, dried and then thermally treated at elevated temperatures from 300° to 700° C., preferably at 350° to 550° C. Reactivation can be undertaken many times; it leads to only slightly reduced metathesis activity in catalysts.

The catalyst system according to the invention is particularly suitable for the metathesis of functionalised olefins, in particular of unsaturated carboxylic acid esters. The catalysts according to the invention can be used as a powder, granulate or as honeycomb structures. The catalysts are preferably used in powder form.

Surprisingly it was found that catalysts comprising ($B_2O_3$ or $WO_3$ or $MoO_3$ or $V_2O_5$)—$Re_2O_7/Al_2O_3$—$SiO_2$+Sn(n-$C_4H_9)_4$ as well as $Re_2O_7/Al_2O_3$—$SiO_2$+Sn(n-$C_4H_9)_4$, each with hydrothermally treated $Al_2O_3$—$SiO_2$ carriers, are clearly more effective than the analogous catalysts with $Al_2O_3$—$SiO_2$ carriers which, to be sure, are made according to the same basic process but have not been subjected to hydrothermal treatment.

The particular significance of hydrothermal treatment of $Al_2O_3$—$SiO_2$ carriers for the activity of $Re_2O_7$ carrier catalysts is to be discussed below by means of comparative experiments.

According to prior art, (cf. EP-B1-0444264) during metathesis of unsaturated carboxylic acid esters, that is of 10-undecylenic acid methyl ester with 4-octens, in the presence of the catalyst $B_2O_3$—$Re_2O_7/Al_2O_3$—$SiO_2$, activated with Sn(n-$C_4H_9)_4$, the lowest catalyst concentrations are stated with a molar ratio of $Re_2O_7:SnR_4$:ester:4-octen= 1:1.2: 800:1600, whereby an ester transformation of 77% was achieved.

Our own trials showed that this catalyst is still effective at even smaller concentrations. To be sure, with a molar ratio of $Re_2O_7$:ester:olefin=1/3000/6000 the transformation is reduced to 41% which is too small for carrying out the reaction in practice (compare example 4). On the other hand, with the $B_2O_3$—$Re_2O_7/Al_2O_3$—$SiO_2$ catalyst (example 3) with hydrothermally treated $Al_2O_3$—$SiO_2$ carrier, under otherwise identical conditions a transformation of almost 70% is achieved.

Even when carrying out the above-mentioned metathesis reaction with the less active $B_2O_3$-free $Re_2O_7$ catalysts ($Re_2O_7/Al_2O_3$—$SiO_2$+$SnBu_4$), the activity-increasing influence of the hydrothermally treated carrier materials is significant. Thus the ester transformation in comparative experiments—here with a molar ratio of 1:1000—increases from 33% (example 6) to 62% (example 5) if the $Al_2O_3$—$SiO_2$ carriers are changed—with the composition otherwise remaining the same—and with a change to hydrothermally treated material. If a $B_2O_3$—, $WO_3$—, $MoO_3$—, or $V_2O_5$—modification is undertaken (example 7, 8 or 9) a further increase in activity to a transformation of more than 75% is achieved.

TABLE 3

Co-metathesis of 10-undecylenic acid methyl ester with 4-octen, examples 3 to 10

| Example | $Re_2O_7$ | $SnBu_4$ [molar ratio] | Ester | 4-octen | [% by weight] | Hydrothermal after-treatment | $C_{11}$-ester [% by weight] | $C_{14}$-ester [% by weight] | $C_{20}$-diester [% by weight] | Transformation [%] |
|---|---|---|---|---|---|---|---|---|---|---|
| 3 | 1 | 1.5 | 3000 | 6000 | 6.4 $B_2O_3$ | X | 30.6 | 62.5 | 6.9 | 66 |
| 4 | 1 | 1.5 | 3000 | 6000 | 6.4 $B_2O_3$ | — | 55.2 | 40 | 4.8 | 41 |
| 5 | 1 | 1.5 | 1000 | 2000 | — | X | 34.3 | 58.8 | 6.9 | 62 |
| 6 | 1 | 1.5 | 1000 | 2000 | — | — | 63.6 | 32.3 | 4.1 | 33 |
| 7 | 1 | 1.5 | 1000 | 2000 | 6.4 $B_2O_3$ | X | 17.0 | 75.2 | 7.8 | 81 |
| 8 | 1 | 1.5 | 1000 | 2000 | 6.4 $WoO_3$ | X | 22.0 | 71.1 | 6.9 | 76 |
| 9 | 1 | 1.5 | 1000 | 2000 | 6.4 $MoO_3$ | X | 18.9 | 75.5 | 5.4 | 78 |
| 10 | 1 | 1.5 | 1000 | 2000 | 6.4 $V_2O_5$ | X | 20.2 | 74.2 | 5.6 | 77 |

Example 11 illustrates the finding of a surprising catalytic reactivation through thermal treatment of previously used rhenium oxide carrier catalysts according to the invention.

EXAMPLE 1

Production of the catalyst $B_2O_3$—$Re_2O_7$ on a hydrothermally treated $Al_2O_3$—$SiO_2$ carrier 10 g hydrothermally treated aluminium silicate ($Al_2O_3$—$SiO_2$) with 20% by weight $SiO_2$ (see table 1) are first calcined in a stream of dried air at 550° C. for 15 hours and then cooled to room temperature under argon. The carrier material thus calcined, together with 0.55 g ammonium perrhenate ($NH_4ReO_4$) and 1.33 boric acid($H_3BO_3$) as well as 90 ml 1.4-dioxane and 10 ml distilled water, are heated for 12 hours under reflux. Then the solvent is distilled off and the remaining, now impregnated $Al_2O_3$—$SiO_2$ carrier is dried at 120° C. in the water jet vacuum and finally—as mentioned above—calcined for 12 hours at 550° C. in the airstream. The $B_2O_3$—$Re_2O_7/Al_2O_3$—$SiO_2$ catalyst produced in this way nominally contains 6.4% by weight $B_2O_3$ and 5% per weight of $Re_2O_7$, in each instance related to the $Al_2O_3$—$SiO_2$ carrier.

EXAMPLE 1a

According to a further example, preferred to example 1, for impregnating the hydrothermally altered aluminium silicate carrier, 1.24 g $NH_4ReO_4$ and 2.58 g $H_3BO_3$ are dissolved in 25 g water at 60° C. This solution is applied to 20 g of hydrothermally altered aluminium silicate (see table 1) e.g. Siral HT2O carrier (product of Condea Chemie GmbH, precalcined at 550° C.), by means of a manual atomiser under intensive mixing. The catalyst impregnated in such a way is activated at 550° C. without any further drying and used in the metathesis. In this example the contact contains nominally 5.0% by weight $Re_2O_7$; 6.4% by weight $B_2O_3$ and 18% by weight $SiO_2$. The difference to 100% is made up of $Al_2O_3$.

EXAMPLE 2

Production of the catalyst $Re_2O_7$ on a hydrothermally treated $Al_2O_3$—$SiO_2$ carrier The catalyst production of example 1 is repeated, except that no boric acid is used. The catalyst $Re_2O_7/Al_2O_3$—$SiO_2$ ($Al_2O_3$—$SiO_2$ hydrothermally treated) results, with 5% by weight $Re_2O_7$ in relation to the $Al_2O_3$—$SiO_2$ carrier which contains 20% by weight $SiO_2$.

EXAMPLE 3

Co-metathesis of 10-undecylenic acid methyl ester with 4-octen catalyst: $B_2O_3$—$Re_2O_7/Al_2O_3$—$SiO_2$ ($Al_2O_3$—$SiO_2$ hydrothermally treated, 20% by weight $SiO_2$), activated with

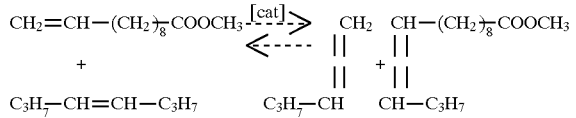

In a baked-out 50 ml glass autoclave filled with argon, stir 0.12 g of the catalyst shown in example 1 (this catalyst quantity contains 0.012 mmol $Re_2O_7$), 0.19 ml of an 0.1 molar stannic butyl solution in cyclohexane (0.019 mmol $Sn(n-C_4H_9)_4$) as well as 7.36 g 10-undecylenic acid methyl ester (37 mmol) and 8.34 g 4-octen (74 mmol) at room temperature with a magnetic core stirrer. The molar ratio of the reaction components was $Re_2O_7:SnBu_4:ester:4-octen=1:1.5:3000:6000$.

After 3 hours the catalyst, in the form of a powder, is separated by centrifuging. A sample is taken from the reaction solution and a few drops of ethanol are added to it in order to destroy any remaining catalyst. Then the sample is gas-chromatographically analysed.

According to the above reaction equation, the reaction solution, apart from the educts, now also contains 1-pentene and 10-tetradecenoic acid methyl ester as well as small quantities of 0-eicosene-1.20-dicarboxylic acid dimethyl ester which was formed by self-metathesis of the 10-undecylenic acid methyl ester, according to

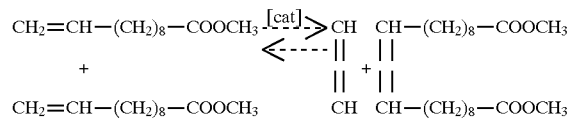

Composition of the esters in the reaction mixture was 30.6% by weight 10-undecylenic acid methyl ester, 62.5% by weight 10-tetradecenoic acid methyl ester and 6.9% by weight $C_{20}$-dicarboxylic acid dimethyl ester. This represents a transformation of 66% of the 10-undecylenic acid methyl ester used.

EXAMPLE 4 (comparative example)

Co-metathesis of 10-undecylenic acid methyl ester with 4-octen

Catalyst: $B_2O_3$—$Re_2O_7/Al_2O_3$—$SiO_2$ (20 by weight $SiO_2$) activated with $Sn(n-C_4H_9)_4$.

The experiment of example 3 is repeated, except that now a catalyst is used for the production of which an aluminium silicate with 20% by weight $SiO_2$ was used (according to example 1), during whose preparation according to DE-C1-38 39 580 there was no hydrothermal treatment, i.e. no thermal after-treatment.

With the same quantities and reaction conditions as in example 3, the transformation of 10-undecylenic acid methyl ester drops to 41%; the ester composition is 55.2% by weight $C_{11}$-ester, 40.0% by weight $C_{14}$-ester and 4.8% by weight $C_{20}$-diester.

EXAMPLE 5

Co-metathesis of 10-undecylenic acid methyl ester with 4-octen

Catalyst: $Re_2O_7/Al_2O_3$—$SiO_2$ ($Al_2O_3$—$SiO_2$ hydrothermally treated, 20% by weight $SiO_2$) activated with $Sn(n-C_4H_9)_4$.

The experiment of example 3 is repeated, except that now the $B_2O_3$-free catalyst made according to example 2 is used and a molar ratio of the reaction components $Re_2O_7:SnBu_4:ester:4-octen=1:1.5:1000:2000$ is applied. After 3 hours at room temperature, a transformation of $C_{11}$-ester of 62% is recorded and the ester composition is 34.3% by weight $C_{11}$-ester, 58.8% by weight $C_{14}$-ester and 6.9% by weight $C_{20}$-diester.

EXAMPLE 6 (comparative example)

Co-metathesis of 10-undecylenic acid methyl ester with 4-octen

Catalyst: $Re_2O_7/Al_2O_3$—$SiO_2$, activated with $Sn(n-C_4H_9)_4$.

The experiment of example 5 is repeated, except that now a catalyst made with an aluminium silicate of 20% by weight $SiO_2$ according to example 2 is used, during whose preparation according to DE-Cl-38 39 580 there was no hydrothermal treatment.

With the same quantities and reaction conditions as in example 5, the transformation of the $C_{11}$-ester drops to 33%; the ester composition is 63.6% by weight $C_{11}$-ester, 32.3% by weight $C_{14}$-ester and 4.1% by weight $C_{20}$-diester.

EXAMPLE 7

Co-metathesis of 10-undecylenic acid methyl ester with 4-octen

Catalyst: $B_2O_3$ $Re_2O_7/Al_2O_3$—$SiO_2$ ($Al_2O_3$—$SiO_2$ hydrothermally treated, 20% by weight $SiO_2$) activated with $Sn(n-C_4H_9)_4$.

Under the same conditions as example 5, i.e. molar ratio $Re_2O_7:SnBu_4:ester:4-octen=1:1.5:1000:2000$, except with catalyst containing $B_2O_3$, from example 1, after 3 hours at room temperature the transformation rises to 81% and the ester composition was 17.0% by weight $C_{11}$-ester, 75.2% by weight $C_{14}$-ester and 7.8% by weight $C_{20}$-diester.

EXAMPLE 8

Co-metathesis of 10-undecylenic acid methyl ester with 4-octen

Catalyst: $WO_3$—$Re_2O_7/Al_2O_3$—$SiO_2$ ($Al_2O_3$—$SiO_2$ hydrothermally treated, 20% by weight $SiO_2$) activated with $Sn(n-C_4H_9)_4$.

Under the same conditions as example 5, i.e. molar ratio $Re_2O_7:SnBu_4:ester:4-octen=1:1.5:1000:2000$, except with catalyst containing $WO_3$, after 3 hours at room temperature the transformation rises to 76% and the ester composition was 22.0% by weight $C_{11}$-ester, 71.1% by weight $C_{14}$-ester and 6.9% by weight diester.

Production of the catalyst took place as described in example 1a, except that instead of $H_3BO_3$, 1.59 g $(NH_4)_{10}W_{12}O_{41}$ was now used. The catalyst contained 5.0% by weight $Re_2O_7$ and 6.4% by weight $WO_3$.

EXAMPLE 9
Co-metathesis of 10-undecylenic acid methyl ester with 4-octen

Catalyst: $MoO_3$—$Re_2O_7/Al_2O_3$—$SiO_2$ ($Al_2O_3$—$SiO_2$ hydrothermally treated, 20% by weight $SiO_2$) activated with $Sn(n-C_4H_9)_4$.

Under the same conditions as example 5, i.e. molar ratio $Re_2O_7:SnBu_4:ester:4-octen=1:1.5:1000:2000$, except with catalyst containing $MoO_3$, after 3 hours at room temperature the transformation rises to 78% and the ester composition was 18.9% by weight $C_{11}$-ester, 75.5% by weight $C_{14}$-ester and 5.4% by weight diester. Production of the catalyst took place as described in example 1a, except that instead of $H_3BO_3$, 1.77 g $(NH_4)_6Mo_7O_{24}$ was now used. The catalyst contained 5.0% by weight $Re_2O_7$ and 6.4% by weight $MoO_3$.

EXAMPLE 10
Co-metathesis of 10-undecylenic acid methyl ester with 4-octen

Catalyst: $V_2O_5$—$Re_2O_7/Al_2O_3$—$SiO_2$ ($Al_2O_3$—$SiO_2$ hydrothermally treated, 20% by weight $SiO_2$) activated with $Sn(n-C_4H_9)_4$.

Under the same conditions as example 5, i.e. molar ratio $Re_2O_7:SnBu_4:ester:4-octen=1:1.5:1000:2000$, except with catalyst containing $V_2O_5$, after 5 hours at room temperature the transformation rises to 77% and the ester composition was 20.2% by weight $C_{11}$-ester, 74.2% by weight $C_{14}$-ester and 5.6% by weight diester.

Production of the catalyst took place as described in example 1, except that instead of $H_3BO_3$, 0.968 g $NaVO_3$ was now used. The catalyst contained 5.0% by weight $Re_2O_7$ and 6.4% by weight $V_2O_5$.

EXAMPLE 11
Co-metathesis of 10-undecylenic acid methyl ester with 4-octen, experiments for catalyst recycling Catalyst: $B_2O_3$—$Re_2O_7/Al_2O_3$—$SiO_2$, ($Al_2O_3$—$SiO_2$ hydrothermally treated), activated with $Sn(n-C_4H_9)_4$.

During production of the catalyst according to example 1, two parameters were varied. Firstly the hydrothermally treated aluminium silicate with 20% by weight $SiO_2$ was used in extrudate form; secondly 10 g calcined carrier material was mixed only with 0.11 g ammonium perrhenate with the quantity of boric acid remaining the same (1.33 g), resulting in a catalyst of nominally 1% by weight $Re_2O_7$. This catalyst was charged into the co-metathesis of 10-undecylenic acid methyl ester with 4-octen; in each instance filtered off after the end of the reaction, dried at 120° C. and after renewed 12-hour activation at 550° C. in the airstream and subsequent $SnBu_4$ addition, tested again in the above metathesis reaction.

In this, the starting point of all experiments was as follows: 0.71 g catalyst; 0.44 ml of an 0.1 molar stannic butyl solution in cyclohexane, 10 g 4-octen and 8.8 g 10-undecylenic acid methyl ester. In each instance, the reaction mix was shaken in a laboratory shaker for 6 hours at room temperature. The molar ratio of the reaction components was $Re_2O_7:SnBu_4:ester:4-octen=1:1.5:3000:6000$.

Reactivation was carried out 14 times without significant loss in activity of the contact used. The transformations achieved in the individual tests are shown in table 4.

TABLE 4

Co-metathesis of 10-undecylenic acid methyl ester with 4-octen, on $B_2O_3$—$Re_2O_7/Al_2O_3$—$SiO_2$ activated with $Sn(n-C_4H_9)_4$. - experiments with catalyst recycling

| | Experiment | | | | | | | |
|---|---|---|---|---|---|---|---|---|
| | 1/1 | 1/2 | 1/3 | 1/4 | 1/5 | 1/6 | 1/7 | 1/8 |
| Reactivation cycle | fresh | 1 | 2 | 3 | 4 | 5 | 6 | 7 |
| U [%] | 72 | 74 | 75 | 69 | 71 | 70 | 70 | 66 |

| | Experiment | | | | | |
|---|---|---|---|---|---|---|
| | 1/9 | 1/10 | 1/11 | 1/12 | 1/13 | 1/14 | 1/15 |
| Reactivation cycle | 8 | 9 | 10 | 11 | 12 | 13 | 14 |
| U [%] | 65 | 64 | 60 | 56 | 64 | 61 | 60 |

We claim:

1. A method for the catalytic metathesis of unsaturated compounds selected from the group consisting of olefins, olefins containing functional groups, and unsaturated carboxylic acid esters, comprising pass the compounds over a rhenium oxide catalyst carried on aluminum silicate carrier, where the aluminum silicate carrier is made from at least one silicon compound that can supply $SiO_2$ and an aluminum compound in an aqueous environment, where the aluminum silicate/water mixture is subjected to a temperature treatment of from 90° to 235° C. for a period of 0.5 to 20 hours.

2. Rhenium oxide catalysts carried on aluminum silicate carriers, comprising aluminum silicate carriers made from at least one silicon compound that can supply $SiO_2$ and an aluminum compound in an aqueous environment, where the aluminum silicate/water mixture is subjected to a temperature treatment of from 90° to 235° C. for a period of 0.5 to 20 hours.

3. The rhenium oxide catalysts of claim 2 where the aluminum silicate/water mixture is subjected to the temperature treatment after the reaction of the silicon compound with the aluminum compound.

4. The rhenium oxide catalysts of claim 2 where the aluminum silicate/water mixture is subjected to the temperature treatment during the reaction of the silicon compound with the aluminum compound.

5. The rhenium oxide catalysts of claim 2 where the temperature treatment is of from 150° to 200° C.

6. The rhenium oxide catalysts of claim 2 where the temperature treatment is for a period of 1 to 5 hours.

7. The rhenium oxide catalysts of claim 2 where the aluminum silicate carriers contain 1.5 to 50% by weight $SiO_2$.

8. The rhenium oxide catalysts of claim 2 where the aluminum silicate carriers contain 5 to 30% by weight $SiO_2$.

9. The rhenium oxide catalysts of claim 2 where the rhenium oxide content is 0.5 to 10% by weight.

10. The rhenium oxide catalysts of claim 2 where the rhenium oxide content is 1 to 5% by weight.

11. The rhenium oxide catalysts of claim 2 further comprising an additional oxide selected from the group consisting of boric oxides, tungsten oxides, molybdenum oxides, and vanadium oxides.

12. The rhenium oxide catalysts of claim 11 where the additional oxide is present in an amount from 2 to 10% by weight.

13. The rhenium oxide catalysts of claim 11 where the additional oxide is present in an amount from 3 to 8% by weight.

14. The rhenium oxide catalysts of claim 2 further comprising a tin alkyl activator.

15. Reactivated rhenium oxide catalysts carried on aluminum silicate carriers, comprising aluminum silicate carriers made from at least one silicon compound that can supply $SiO_2$ and an aluminum compound in an aqueous environment, where the aluminum silicate/water mixture is subjected to a temperature treatment of from 90° to 235° C. for a period of 0.5 to 20 hours, and where the rhenium oxide catalysts on aluminum silicate carriers were reactivated after use by a process comprising separating, drying, then thermally treating the catalyst at elevated temperatures from 300° to 700° C.

16. The reactivated rhenium oxide catalysts of claim 15 where the elevated temperatures for thermally treating the used catalyst are from 350° to 550° C.

17. A method of making rhenium oxide catalysts on aluminum silicate carriers, the method comprising reacting at least one silicon compound that can supply $SiO_2$ and an aluminum compound in an aqueous environment; and subjecting the aluminum silicate/water mixture to a temperature treatment of from 90° to 235° C. for a period of 0.5 to 20 hours.

18. The method of claim 17 where subjecting the aluminum silicate/water mixture to the temperature treatment occurs after the reaction of the silicon compound with the aluminum compound.

19. The method of claim 17 where subjecting the aluminum silicate/water mixture to the temperature treatment occurs during the reaction of the silicon compound with the aluminum compound.

* * * * *